US012594380B2

(12) United States Patent
Olds

(10) Patent No.: US 12,594,380 B2
(45) Date of Patent: Apr. 7, 2026

(54) MEDICATION INJECTOR ASSEMBLY AND METHOD OF USE

(71) Applicant: Isaiah Olds, Greensburg, IN (US)

(72) Inventor: Isaiah Olds, Greensburg, IN (US)

( * ) Notice: Subject to any disclaimer, the term of this patent is extended or adjusted under 35 U.S.C. 154(b) by 740 days.

(21) Appl. No.: 18/101,311

(22) Filed: Jan. 25, 2023

(65) Prior Publication Data

US 2024/0245861 A1     Jul. 25, 2024

(51) Int. Cl.
*A61M 5/24*          (2006.01)
*A61M 5/315*         (2006.01)

(52) U.S. Cl.
CPC .......... *A61M 5/24* (2013.01); *A61M 5/31535* (2013.01)

(58) Field of Classification Search
CPC .. A61M 5/24; A61M 5/31535; A61M 5/2455; A61M 5/285; A61M 5/3146; A61M 5/31513; A61M 2005/3118; A61M 2005/312; A61M 2005/3123; A61M 2005/31516
See application file for complete search history.

(56) References Cited

U.S. PATENT DOCUMENTS

| | | | |
|---|---|---|---|
| 8,556,866 | B2 | 10/2013 | Krulevitch |
| 8,591,477 | B2 | 11/2013 | Hieb |
| 8,708,957 | B2 | 4/2014 | Jespersen |
| 9,457,151 | B2 | 10/2016 | Tan |
| 2006/0106362 | A1 | 5/2006 | Pass |
| 2015/0246179 | A1 | 9/2015 | Zur |
| 2016/0175523 | A1 | 6/2016 | Blomberg |
| 2023/0147715 | A1* | 5/2023 | Tillack ................ A61M 5/2448 604/87 |

FOREIGN PATENT DOCUMENTS

WO      WO2009083600      7/2009

* cited by examiner

*Primary Examiner* — Tasnim Mehjabin Ahmed

(57)          ABSTRACT

A medication injector assembly allowing for bubble removal without loss of liquid medicine includes a tubular body fitted containing a cartridge proximate to its first end, to which a needle is selectively attachable so that the needle is in fluidic communication with the cartridge. A plunger and an actuator, which are operationally engaged, are positioned in the tubular body. The actuator is positioned to selectively motivate a stopper of the plunger incrementally through the cartridge to dispense a dose of a liquid medicine from the cartridge through the needle. A valve is positioned in a sidewall of the tubular body proximate to its second end. A tube extends from the valve through the stopper so that the valve is in fluidic communication with the cartridge. Air that is adjacent to the stopper passes through the tube to remove the air from the liquid medicine.

15 Claims, 4 Drawing Sheets

MEDICATION INJECTOR ASSEMBLY AND METHOD OF USE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to injector pens and more particularly pertains to a new injector pen allowing for bubble removal without loss of liquid medicine. The present invention discloses an injector pen having a valve that allow for release of air bubbles.

(2) Description of Related Art Including Information Disclosed Under 37 CFR 1.97 and 1.98

The prior art relates to injector pens, many of which are known. However, the prior art does not teach an injector pen having valve positioned in its sidewall, with a tube extending from the valve through a stopper of the injector pen to its. The tube is configured for passage of air adjacent to the stopper to remove the air from liquid medicine in the cartridge.

BRIEF SUMMARY OF THE INVENTION

An embodiment of the disclosure meets the needs presented above by generally comprising a tubular body, which is configured for insertion of, or permanently fitted with, a cartridge. The cartridge is positioned proximate to a first end of the tubular body. The first end is configured for selective attachment of a needle so that the needle is in fluidic communication with the cartridge. A plunger and an actuator, which are operationally engaged, are positioned in the tubular body. The actuator is positioned to selectively motivate a stopper of the plunger incrementally through the cartridge to dispense a dose of a liquid medicine from the cartridge through the needle. A valve is positioned in a sidewall of the tubular body proximate to a second end of the tubular body. A tube extends from the valve through the stopper so that the valve is in fluidic communication with the cartridge. The tube is configured for passage of air adjacent to the stopper to remove the air from the liquid medicine.

Another embodiment of the disclosure includes a medication injector system, which comprises the medication injector assembly, as disclosed above, which has a cartridge containing a liquid medicine positioned in the tubular body proximate to it first end. A needle is attached to the first end such that the needle is in fluidic communication with the cartridge.

Yet another embodiment of the disclosure includes a method of removing air from a cartridge of liquid medicine, which has provision step entails providing a cartridge containing a liquid medicine, providing a needle, and providing a medication injector assembly, according to the disclosure above. Operational steps entail positioning a cartridge in the tubular body, affixing a needle to the tubular body, positioning the tubular body first end down and tapping the tubular body so that air in the cartridge collects adjacent to the stopper, opening the valve to allow passage of the air from the cartridge through the tube, and closing the valve.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figures 1, 2:
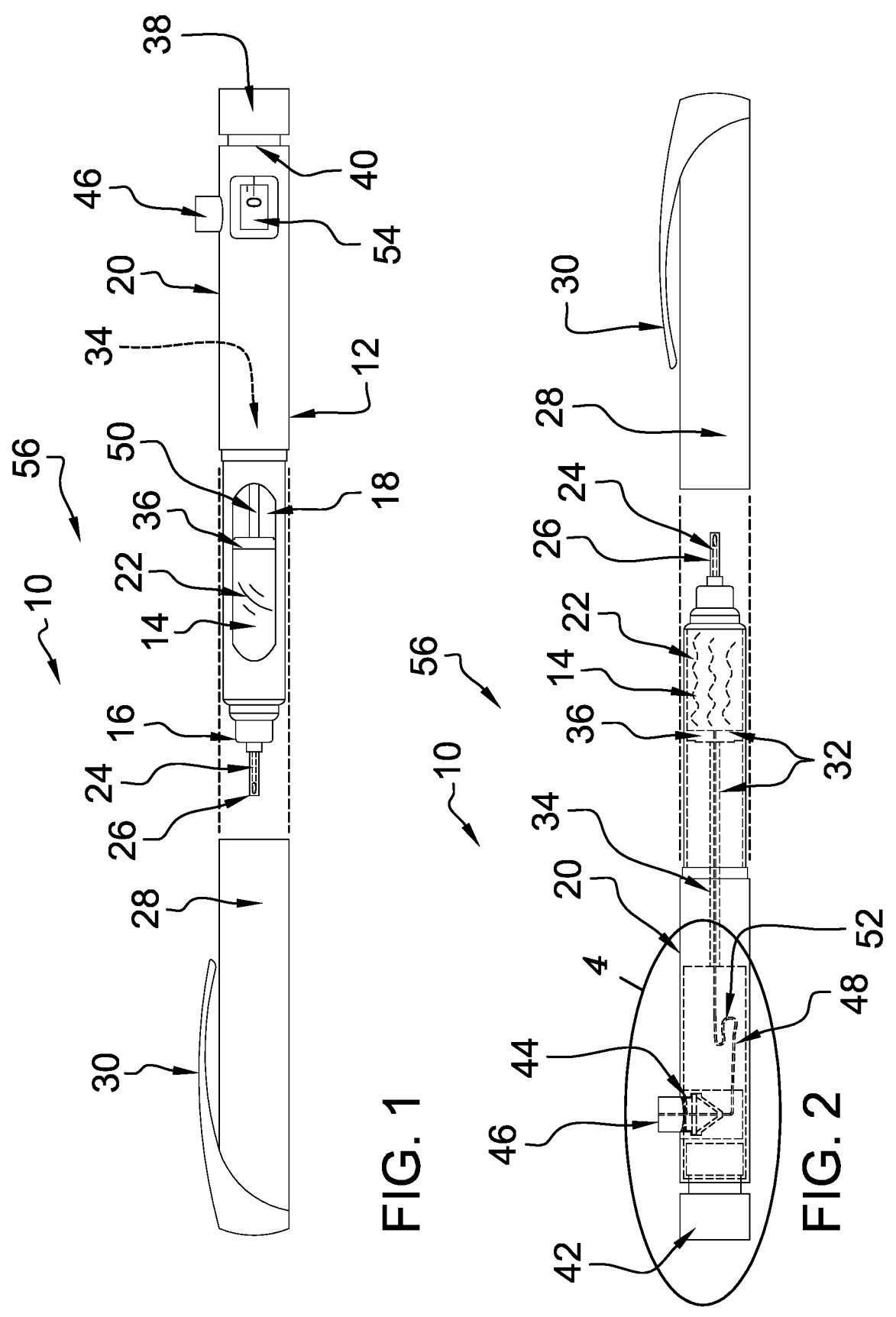
FIG. 1 is a front view of a medication injector assembly according to an embodiment of the disclosure.
FIG. 2 is a rear view of an embodiment of the disclosure.
Figure 3:
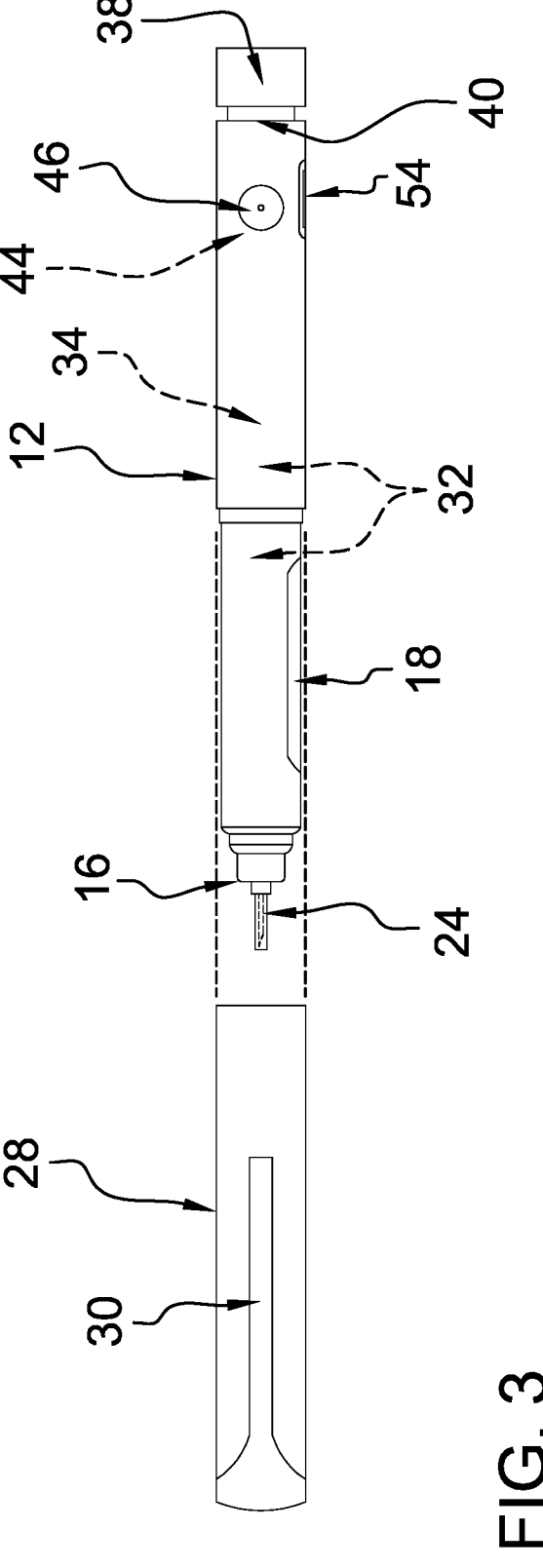
FIG. 3 is a top view of an embodiment of the disclosure.

With reference now to the drawings, and in particular to FIGS. 1 through 5 thereof, a new injector pen embodying the principles and concepts of an embodiment of the disclosure and generally designated by the reference numeral 10 will be described.

As best illustrated in FIGS. 1 through 5, the medication injector assembly 10 generally comprises a tubular body 12, which is configured for insertion of, or permanently fitted with, a cartridge 14. The cartridge 14 is positioned proximate to a first end 16 of the tubular body 12. An opening 18 is positioned in a sidewall 20 of the tubular body 12 proximate to its first end 16. The opening 18 is configured to allow for viewing a liquid medicine 22 and air (bubbles)

in the cartridge 14. The opening 18 may be covered with substantially transparent material, such as glass, plastic, or the like.

The first end 16 is configured for selective attachment of a needle 24 so that the needle 24 is in fluidic communication with the cartridge 14. Such needles 24 are sterile and typically would be provided with a needle cap 26 that is removed immediately prior to use.

The medication injector assembly 10 also may include an endcap 28, into which the first end 16 of the tubular body 12 is insertable to cover the opening 18 and a needle 24 that may be attached to the first end 16. The endcap 28 is selectively attachable to the tubular body 12 and may be fitted with a clip 30 to allow attachment of the medication injector assembly 10 to a pocket in which it is positioned.

Figure 4:
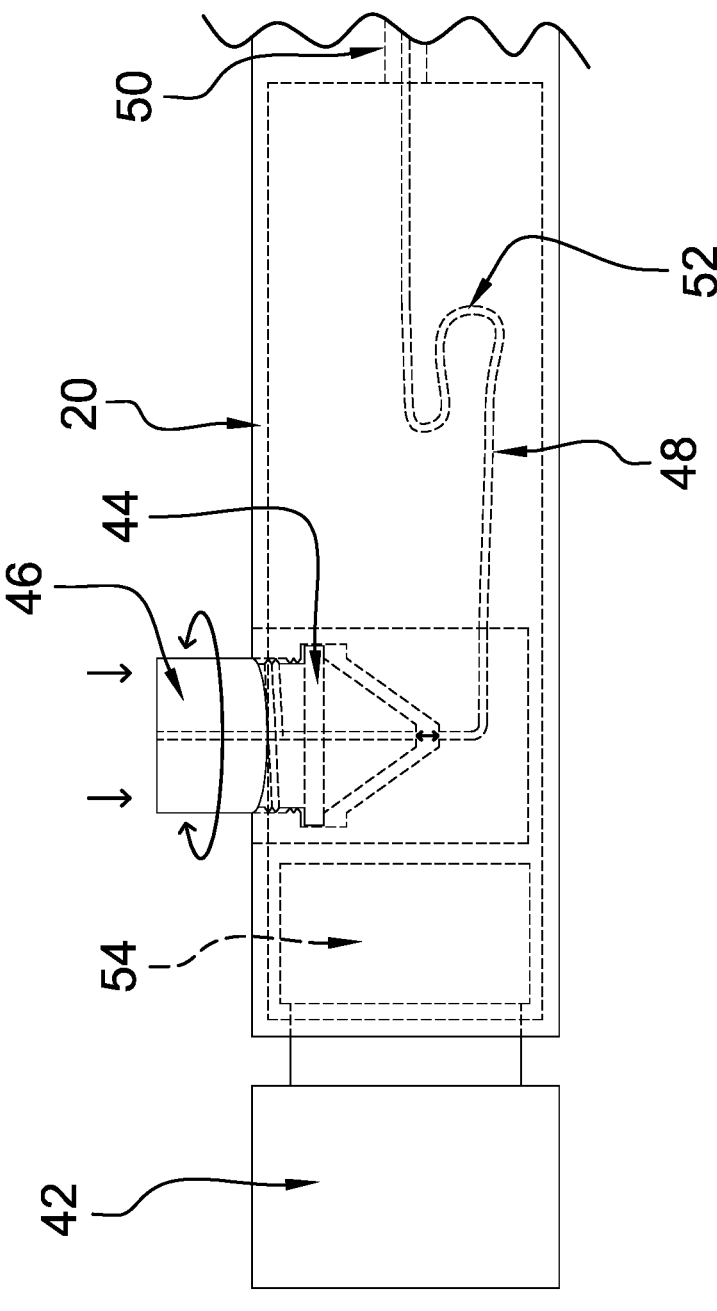
FIG. 4 is a detail view of an embodiment of the disclosure.
Figure 5:
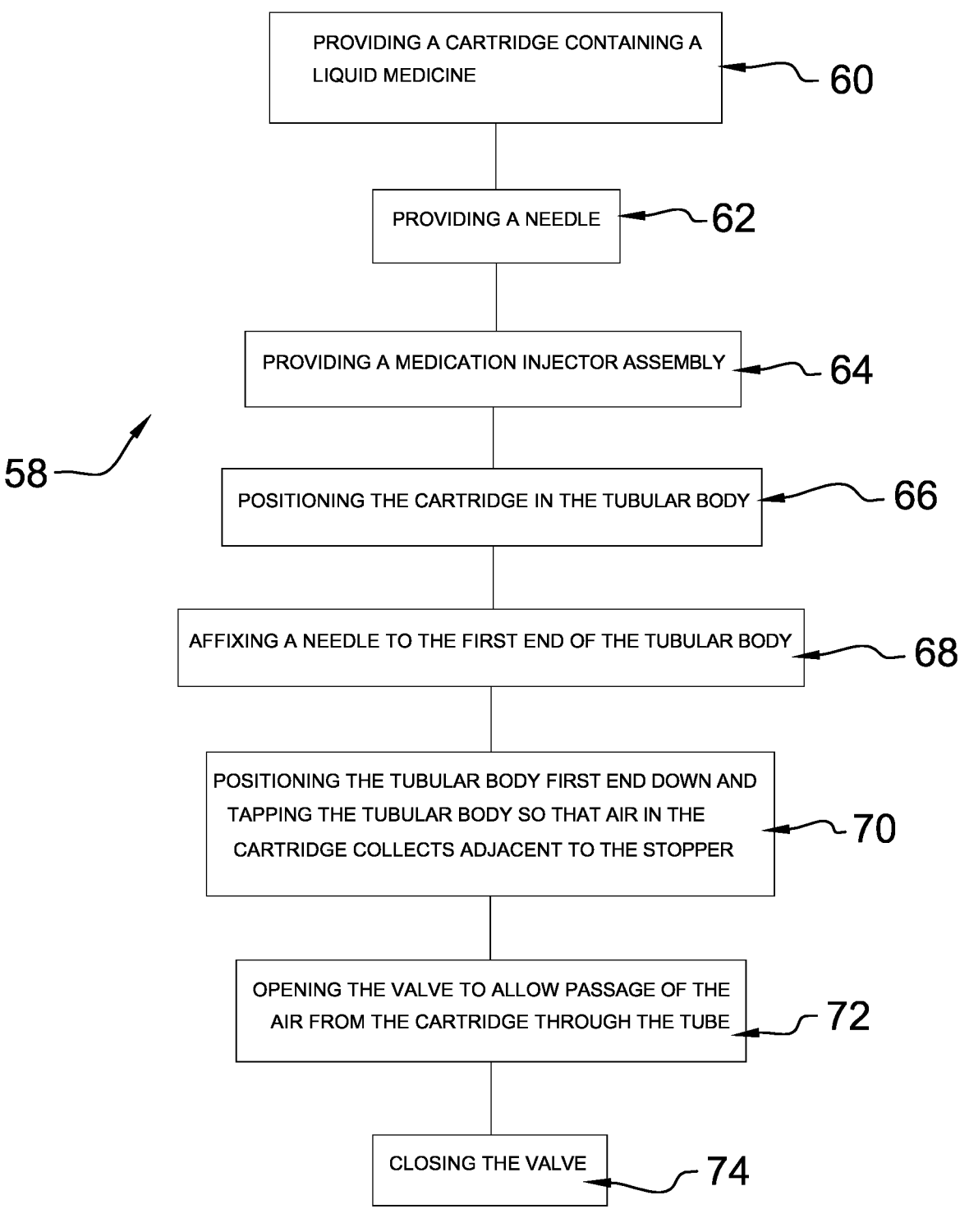
FIG. 5 is a flow diagram for a method utilizing an embodiment of the disclosure.

A plunger 32 and an actuator 34, which are operationally engaged, are positioned in the tubular body 12. The present invention anticipates the actuator 34 being either manual or battery powered. The actuator 34 is positioned to selectively motivate a stopper 36 of the plunger 32 incrementally through the cartridge 14 to dispense a dose of the liquid medicine 22 from the cartridge 14 through the needle 24. A controller 38 is attached to a second end 40 of the tubular body 12 and is operationally engaged to the actuator 34. The controller 38 is configured to be manipulated by a user to actuate the actuator 34 to dispense a dose of the liquid medicine 22. The controller 38 may comprise a pushbutton 42, as shown in FIG. 4, although other controlling means known to those skilled in the art of injector pens are anticipated by the present invention.

A valve 44 is positioned in the sidewall 20 of the tubular body 12 proximate to its second end 40. A knob 46 is attached to the valve 44 and extends from the tubular body 12. The knob 46 is configured to be selectively manipulated by a user to open and to close the valve 44. For example, the knob 46 may be rotatable counterclockwise to open the valve 44 and clockwise to close the valve 44, as shown in FIG. 4. The present invention also anticipates the knob 46 being nonrotatable, but depressible and spring loaded. Pushing of the knob 46 then would open the valve 44 and while releasing of the knob 46 would close the valve 44.

A tube 48 extends from the valve 44 through the stopper 36 so that the valve 44 is in fluidic communication with the cartridge 14. As shown in FIG. 2, the tube 48 extends through a rod 50 of the plunger 32. A loop 52 is positioned in the tube 48 so that the tube 48 is extensible as the stopper 36 is motivated through the cartridge 14. The tube 48 is configured for passage of air adjacent to the stopper 36 to remove the air from the liquid medicine 22. Removal of air from the cartridge 14 is desirable prior to injection.

The medication injector assembly 10 also may comprise a dose counter 54, which is attached to the tubular body 12 and which is operationally engaged to the actuator 34. The dose counter 54 is enabled for keeping and displaying a count of the number of doses that are dispensed from the cartridge 14. The present invention anticipates the dose counter 54 to be deactivated should the actuator 34 be utilized to force the air through the tube 48.

The present invention anticipates a medication injector system 56, which comprises the medication injector assembly 10, as described in the specification above, which has a cartridge 14 containing a liquid medicine 22 positioned in the tubular body 12 proximate to its first end 16. A needle 24 is attached to the first end 16 such that the needle 24 is in fluidic communication with the cartridge 14. The cartridge 14 of the medication injector system 56 may be replaceable and the liquid medicine 22 may comprise insulin.

In use, the medication injector assembly 10 enables a method of removing air from a cartridge of liquid medicine 58. The method 58 comprises a first provision step 60, which entails providing a cartridge 14 that contains a liquid medicine 22. A second provision step 62 of the method 58 is providing a needle 24. A third provision step 64 of the method 58 is providing a medication injector assembly 10, according to the specification above.

A first operational step 66 of the method 58 is positioning the cartridge 14 in the tubular body 12. A second operational step 68 of the method 58 affixing a needle 24 to the first end 16 of the tubular body 12. A third operational step 70 of the method 58 is positioning the tubular body 12 first end 16 down and tapping the tubular body 12 so that air in the cartridge 14 collects adjacent to the stopper 36. A fourth operational step 72 of the method 58 is opening the valve 44 to allow passage of the air from the cartridge 14 through the tube 48. A fifth operational step 74 of the method 58 is closing the valve 44.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A medication injector assembly comprising:
a tubular body configured for insertion of, or permanently fitted with, a cartridge, such that the cartridge is positioned proximate to a first end of the tubular body, the first end being configured for selective attachment of a needle, such that the needle is in fluidic communication with the cartridge;
a plunger positioned in the tubular body;
an actuator positioned in the tubular body and being operationally engaged to the plunger, such that the actuator is positioned for selectively motivating a stopper of the plunger incrementally through the cartridge for dispensing a dose of a liquid medicine from the cartridge through the needle;
a valve positioned in a sidewall of the tubular body proximate to a second end of the tubular body; and
a tube extending from the valve through the stopper, such that the valve is in fluidic communication with the cartridge, wherein the tube is configured for passage of air adjacent to the stopper for removing the air from the liquid medicine.

2. The medication injector assembly of claim 1, further including an opening positioned in the sidewall proximate to the first end of the tubular body, wherein the opening is configured for viewing the liquid medicine and air in the cartridge.

3. The medication injector assembly of claim 2, further including an endcap into which the first end of the tubular body is insertable for covering the opening and a needle that may be attached to the first end, the endcap being selectively attachable to the tubular body.

4. The medication injector assembly of claim 1, further including a controller attached to the second end of the tubular body and being operationally engaged to the actuator, wherein the controller is configured for being manipulated by a user for actuating the actuator for dispensing a dose of the liquid medicine.

5. The medication injector assembly of claim 4, wherein the controller comprises a pushbutton.

6. The medication injector assembly of claim 1, further including a knob attached to the valve and extending from the tubular body, wherein the knob is configured for being selectively manipulated by a user for opening and closing the valve.

7. The medication injector assembly of claim 6, wherein the knob is rotatable counterclockwise for opening the valve and clockwise for closing the valve.

8. The medication injector assembly of claim 1, wherein the tube extends through a rod of the plunger.

9. The medication injector assembly of claim 8, further including a loop positioned in the tube, such that the tube is extensible as the stopper is motivated through the cartridge.

10. The medication injector assembly of claim 1, further including a dose counter attached to the tubular body and operationally engaged to the actuator, such that the dose counter is enabled for keeping and displaying a count of the number of doses dispensed from the cartridge.

11. The medication injector assembly of claim 1, further including:

an opening positioned in the sidewall proximate to the first end of the tubular body, wherein the opening is configured for viewing the liquid medicine and air in the cartridge;

an endcap into which the first end of the tubular body is insertable for covering the opening and a needle that may be attached to the first end, the endcap being selectively attachable to the tubular body;

a controller attached to the second end of the tubular body and being operationally engaged to the actuator, wherein the controller is configured for being manipulated by a user for actuating the actuator for dispensing a dose of the liquid medicine, the controller comprising a pushbutton;

a knob attached to the valve and extending from the tubular body, wherein the knob is configured for being selectively manipulated by a user for opening and closing the valve, the knob being rotatable counterclockwise for opening the valve and clockwise for closing the valve;

the tube extending through a rod of the plunger;

a loop positioned in the tube, such that the tube is extensible as the stopper is motivated through the cartridge; and a dose counter attached to the tubular body and operationally engaged to the actuator, such that the dose counter is enabled for keeping and displaying a count of the number of doses dispensed from the cartridge.

12. A medication injector system comprising:
a tubular body;
a cartridge positioned in the tubular body proximate to a first end of the tubular body;
a liquid medicine positioned in the cartridge;
a needle attached to the first end such that the needle is in fluidic communication with the cartridge;
a plunger positioned in the tubular body;
an actuator positioned in the tubular body and being operationally engaged to the plunger, such that the actuator is positioned for selectively motivating a stopper of the plunger incrementally through the cartridge for dispensing a dose of the liquid medicine from the cartridge through the needle;
a valve positioned in a sidewall of the tubular body proximate to a second end of the tubular body; and
a tube extending from the valve through the stopper, such that the valve is in fluidic communication with the cartridge, wherein the tube is configured for passage of air adjacent to the stopper for removing the air from the liquid medicine.

13. The medication injector system of claim 12, wherein the cartridge is replaceable.

14. The medication injector system of claim 12, wherein liquid medicine comprises insulin.

15. A method of removing air from a cartridge of liquid medicine comprising the steps of:
providing a cartridge containing a liquid medicine;
providing a needle;
providing a medication injector assembly comprising:
a tubular body configured for insertion of the cartridge, such that the cartridge is positioned proximate to a first end of the tubular body, the first end being configured for selective attachment of a needle, such that the needle is in fluidic communication with the cartridge,
a plunger positioned in the tubular body,
an actuator positioned in the tubular body and being operationally engaged to the plunger, such that the actuator is positioned for selectively motivating a stopper of the plunger incrementally through the cartridge for dispensing a dose of a liquid medicine from the cartridge through the needle,
a valve positioned in a sidewall of the tubular body proximate to a second end of the tubular body, and
a tube extending from the valve through the stopper, such that the valve is in fluidic communication with the cartridge, wherein the tube is configured for passage of air adjacent to the stopper for removing the air from the liquid medicine;
positioning the cartridge in the tubular body;
affixing a needle to the first end of the tubular body;
positioning the tubular body first end down and tapping the tubular body so that air in the cartridge collects adjacent to the stopper;
opening the valve to allow passage of the air from the cartridge through the tube; and
closing the valve.

* * * * *